United States Patent
Shimizu et al.

(10) Patent No.: US 10,240,172 B2
(45) Date of Patent: Mar. 26, 2019

(54) METHOD FOR PRODUCING HIGH PURITY OMEGA-3 FATTY ACID ETHYL ESTER

(71) Applicant: Bizen Chemical Co., Ltd., Okayama (JP)

(72) Inventors: Yoshio Shimizu, Okayama (JP); Keisuke Uryu, Okayama (JP); Tetsuro Taira, Okayama (JP); Jun Fujii, Okayama (JP)

(73) Assignee: Bizen Chemical Co., Ltd., Akaiwa-shi, Okayama (JP)

( * ) Notice: Subject to any disclaimer, the term of this patent is extended or adjusted under 35 U.S.C. 154(b) by 122 days.

(21) Appl. No.: 14/914,804

(22) PCT Filed: Aug. 18, 2014

(86) PCT No.: PCT/JP2014/004209
§ 371 (c)(1),
(2) Date: Feb. 26, 2016

(87) PCT Pub. No.: WO2015/029364
PCT Pub. Date: Mar. 5, 2015

(65) Prior Publication Data
US 2016/0208296 A1 Jul. 21, 2016

(30) Foreign Application Priority Data

Aug. 30, 2013 (JP) ................................ 2013-179769
Mar. 20, 2014 (JP) ................................ 2014-058816

(51) Int. Cl.
| | | |
|---|---|---|
| C12P 7/64 | (2006.01) | |
| C07C 67/03 | (2006.01) | |
| C07C 67/08 | (2006.01) | |
| C07C 67/54 | (2006.01) | |
| C07C 67/56 | (2006.01) | |
| C07C 67/60 | (2006.01) | |
| C11C 1/08 | (2006.01) | |
| C11C 1/10 | (2006.01) | |
| C11C 3/00 | (2006.01) | |
| C11C 3/04 | (2006.01) | |
| C11B 1/02 | (2006.01) | |
| C11B 3/10 | (2006.01) | |
| C11B 3/12 | (2006.01) | |
| C11B 5/00 | (2006.01) | |

(52) U.S. Cl.
CPC ............ *C12P 7/6427* (2013.01); *C07C 67/03* (2013.01); *C07C 67/08* (2013.01); *C07C 67/54* (2013.01); *C07C 67/56* (2013.01); *C07C 67/60* (2013.01); *C11B 1/025* (2013.01); *C11B 3/10* (2013.01); *C11B 3/12* (2013.01); *C11B 5/0021* (2013.01); *C11C 1/08* (2013.01); *C11C 1/10* (2013.01); *C11C 3/003* (2013.01); *C11C 3/04* (2013.01)

(58) Field of Classification Search
None
See application file for complete search history.

(56) References Cited

U.S. PATENT DOCUMENTS

| 5,679,809 A | 10/1997 | Bertoli et al. |
| 5,945,318 A * | 8/1999 | Breivik .................. C07C 67/60 435/134 |

FOREIGN PATENT DOCUMENTS

| EP | 2172558 A1 | 4/2010 |
| EP | 2330177 A1 | 6/2011 |
| WO | 94/2552 A1 | 11/1994 |
| WO | WO 00/73254 | * 12/2000 |

OTHER PUBLICATIONS

Hangzhou YongSheng Catalyst Co. Ltd, "About us". 2009, 2 pages.*
Alibaba "Acid Activated White Earth Clay for oil Refining Bleaching Decoloring Recycling" 4 pgs, 1999-2018 (Year: 1999).*
Louis L. Richardson "Use of Bleaching, Clays, in Processing Edible Oils" Journal of the American Oil Chemists' Society 55(11):777-780 • Nov. 1978 (Year: 1978).*

* cited by examiner

*Primary Examiner* — Thane Underdahl
(74) *Attorney, Agent, or Firm* — Seed IP Law Group LLP

(57) ABSTRACT

The present invention relates to the field of methods for purifying fatty acid ethyl esters. According to the present invention, a method for obtaining a ω3 fatty acid ethyl ester, such as EPA and DHA, each as a high purity product at a high yield is provided. In the method according to the present invention, a raw material fat including EPA and DHA is treated with a lipolytic enzyme and ethyl-esterification is performed as needed; the treated substance is fractionated into a glyceride fraction and a free fatty acid fraction; a fraction comprising more EPA ester and a fraction comprising DHA ester are obtained from the respective fractions; the fraction comprising more EPA ester is purified to prepare a high-purity EPA ester; and the fraction comprising more DHA ester is purified to prepare a high-purity DHA ester.

17 Claims, No Drawings

METHOD FOR PRODUCING HIGH PURITY OMEGA-3 FATTY ACID ETHYL ESTER

TECHNICAL FIELD

The present invention relates to an industrial production method for obtaining eicosapentaenoic acid (hereinafter, referred to as "EPA") and/or docosahexaenoic acid (hereinafter, referred to as "DHA") from a raw material fat comprising EPA and/or DHA or other omega 3 fatty acids (hereinafter, referred to as "ω3 fatty acid") at a yield higher than prior art.

BACKGROUND ART

ω3 fatty acids, EPA and DHA, have a variety of physiological actions against circulatory diseases, neurotransmission diseases and the like, and they are used as drugs, health food, food ingredients, feed and the like. For example, a high purity EPA ethyl ester of 90 wt % or more is used as a therapeutic agent for arterial sclerosis and hyperlipidemia. In addition, beverages containing EPA or DHA are approved as food for specified health use. Glyceride and ethyl ester of EPA and DHA are utilized as dietary supplement throughout the world.

Marine fats, such as fish oil, marine algae fat and single-celled algae fat, containing EPA, DHA or other ω3 fatty acids, have a variety of types of raw material-derived impurities in addition to gum substances, phospholipids and free fatty acids, and mainly glyceride of fatty acids. EPA and DHA are mostly present therein in the form of glyceride. Most of EPA and DHA are bound to position 2 of glyceride. These marine fats are degummed or deacidified (Non-Patent Document 1) using a publicly known method.

For concentration and purification of EPA and DHA of glyceride bodies, a low-temperature solvent fractional crystallization method and a wintering method are generally used, but their efficiency for concentration is low. Thus, such techniques are often industrially used to efficiently concentrate EPA and DHA in the form of glyceride using lipase, which specifically hydrolyzes fatty acids other than the EPA or DHA bound to position 1 or 3 of the glyceride (Patent Document 1). Furthermore, in order to increase productivity, addition of reactive additives such as calcium hydroxide and magnesium chloride to reaction systems (Patent Document 2) and addition of polar solvents including lower alcohol (Patent Document 3) have been proposed.

In order to obtain higher purity EPA and DHA, a technique such as, firstly ethyl-esterifying fatty acids bound to glyceride to form a monomer is performed. As for the ethyl-esterifying step, publicly known are an enzymatic method as well as an acid catalytic method, an alkali catalytic method and the like (Patent Document 4, Non-Patent Document 2).

Highly-unsaturated fatty acids such as EPA and DHA in fat, including ethyl-esterified ω3 fatty acids, are purified at a relatively high purity using a combination method of one or more of urea addition method (Patent Documents 5 and 6), a silver nitrate complex method (Patent Documents 7 and 8), a vacuum precision distillation method including a vacuum thin-film distillation method (Patent Document 9), a chromatography method such as liquid chromatography (hereinafter, referred to as HPLC) or simulated moving bed chromatography method (Patent Document 9), and the like.

Activated charcoal, activated white earth, acid white earth, silica gel, alumina and the like are used to remove impurity components, such as foreign substances mixed during manufacture, peroxides, colored substances and odor components, from the thus-obtained high purity ω3 fatty acid ethyl esters such as EPA and DHA (Patent Documents 10 to 12).

The thus-produced high purity ω3 fatty acid ethyl esters such as EPA and DHA are produced and used as health food and drugs throughout the world, and their market currently continues to expand.

In the case of obtaining a ω3 fatty acid ethyl ester such as each of EPA and DHA as a high purity product at a high yield from a mixture of marine fat ethyl esters using prior art, for example, in the case of preparing an EPA ethyl ester of 70 wt % or more, it is necessary to remove contaminants such as all-cis-6,9,12,15-octadecatrienoic acid (18:4ω3; hereinafter, referred to as "SDA") and DHA ethyl esters, having physicochemical characteristics similar to EPA ethyl esters. However, the removal of these matters is generally difficult, and if the reduction of these contaminants is aimed, then there will be a technical problem of reduction in the yield of the final products.

In addition, in the case of preparing a DHA ethyl ester of 70 wt % or more, the removal of SDA ethyl esters and EPA ethyl esters becomes difficult, and thus there is a technical problem of causing the reduction in the yield of final products in a similar manner.

There is a need to provide a technique of removing contaminant components including SDA in an efficient manner in order to obtain ω3 fatty acid ethyl esters such as EPA and DHA as high purity products at a high yield.

PRIOR ART DOCUMENTS

Patent Documents

Patent Document 1: Japanese Laid-Open Publication No. 2002-69475
Patent Document 2: Japanese Laid-Open Publication No. 2013-5589
Patent Document 3: Japanese Laid-Open Publication No. 2013-121366
Patent Document 4: Japanese Laid-Open Publication No. 2006-288228
Patent Document 5: Japanese Laid-Open Publication No. 2007-89522
Patent Document 6: Japanese National Phase PCT Laid-open Publication No. 2009-504588
Patent Document 7: Japanese Laid-Open Publication No. 2010-64974
Patent Document 8: Japanese Laid-Open Publication No. 7-242895
Patent Document 9: Japanese Laid-Open Publication No. 11-209786
Patent Document 10: Japanese Laid-Open Publication No. 6-72959
Patent Document 11: Japanese National Phase PCT Laid-open Publication No. 2003-516466
Patent Document 12: Japanese Laid-Open Publication No. 2003-313578

Non-Patent Documents

Non-Patent Document 1: Kosaku YASUDA et al., Yushiseihin no chishiki, Saiwai Shobou (Tokyo), 1977, pp. 103-104
Non-Patent Document 2: Yushikagaku Binran, 4th edition, Japan Oil Chemists' Society, Maruzen (Tokyo), 2001, pp. 454-456

SUMMARY OF INVENTION

Problem to be Solved by the Invention

The problem to be solved by the present invention is to provide a method for obtaining a ω3 fatty acid ethyl ester, such as EPA and DHA, each as a high purity product at a high yield.

Means for Solving the Problem

We found that in the case of purifying highly-unsaturated fatty acids such as EPA and DHA in fat, including ethyl-esterified ω3 fatty acids, at a high purity (for example, in the case of purifying highly-unsaturated fatty acids at a high purity using a combination method of one or more of a urea addition method, a silver nitrate complex method, a vacuum precision distillation method, a chromatography method and the like), when the fat is treated in advance with a lipolytic enzyme to divide a glyceride fraction (fraction including a large number of glycerin fatty acid esters) from a free fatty acid fraction (wherein the free fatty acid fraction may be an ethyl-esterified fraction or a non-ethyl-esterified fraction), each fraction is ethyl-esterified as needed, followed by further purifying to prepare a fraction having a smaller ratio of other fatty acid esters or glycerin fatty acid esters with respect to a target substance (substance in which a fatty acid portion of the target fatty acid ethyl ester or glycerin fatty acid ester is ethyl-esterified), so that the target substance with a higher yield can be obtained, thereby achieving the present invention. For example, according to the present invention, fat is treated with a lipolytic enzyme followed by ethyl-esterification as needed and dividing an ethyl-esterified glyceride fraction (wherein the fatty acid portion of a glycerin fatty acid ester is ethyl-esterified) from an ethyl-esterified free fatty acid fraction; the ethyl-esterified glyceride fraction is divided into (1) a fraction including more DHA than EPA and (2) a fraction including more EPA than DHA; the ethyl-esterified free fatty acid fraction is divided into (3) a fraction including more DHA than EPA and (4) a fraction including more EPA than DHA; a mixture in which (1) and (3) are mixed and a mixture in which (2) and (4) are mixed are prepared respectively; and these mixtures are further purified, thereby obtaining a high purity EPA purified product, and a high purity DHA purified product. For example, according to the present invention, fat is treated in advance with a lipolytic enzyme under conditions for ethyl-esterifying fatty acids (mainly under conditions for ethyl-esterifying free fatty acids), a glyceride fragment is divided from an ethyl-esterified free fatty acid fraction; the glyceride fraction is ethyl-esterified, and the ethyl-esterified glyceride fraction (wherein the fatty acid portion of the glycerin fatty acid ester is mainly ethyl-esterified) is divided into (1) a fraction including more DHA than EPA and (2) a fraction including more EPA than DHA; the ethyl-esterified free fatty acid fraction is divided into (3) a fraction including more DHA than EPA and (4) a fraction including more EPA than DHA; a mixture in which (1) and (3) are mixed and a mixture in which (2) and (4) are mixed are prepared respectively; and these mixtures are further purified, thereby obtaining a high purity EPA purified product, and a high purity DHA purified product. For example, according to the present invention, fat is treated in advance with a lipolytic enzyme, a glyceride fragment is divided from a free fatty acid fraction; the respective fractions are ethyl-esterified; the ethyl-esterified glyceride fraction (wherein the fatty acid portion of the glycerin fatty acid ester is mainly ethyl-esterified) is divided into (1) a fraction including more DHA than EPA and (2) a fraction including more EPA than DHA; the ethyl-esterified free fatty acid fraction is divided into (3) a fraction including more DHA than EPA and (4) a fraction including more EPA than DHA; a mixture in which (1) and (3) are mixed and a mixture in which (2) and (4) are mixed are prepared respectively; and these mixtures are further purified, thereby obtaining a high purity EPA purified product, and a high purity DHA purified product.

For example, according to the present invention, at a step prior to the purification at a higher purity using a combination method of one or more of a urea addition method, a silver nitrate complex method, a vacuum precision distillation method, a chromatography method and the like, a marine fat-derived glyceride fraction or free fatty acid fraction, in which the EPA purity or DHA purity is increased by enzymic treatment and in which the ratio of the other fatty acids, including SDA, is decreased, is used as a starting material, so that the yield of the products can be increased. For example, according to the present invention, one of the features of the present invention is to increase the yield of the target component by decreasing the ratio of DHA or SDA with respect to EPA to obtain a high purity EPA, or by decreasing the ratio of EPA or SDA with respect to DHA to purify a high purity DHA.

The present invention provides, for example, the following:
(Item 1)

A method for preparing an eicosapentaenoic acid ethyl ester and a docosahexaenoic acid ethyl ester from a raw material fat comprising eicosapentaenoic acid and docosahexaenoic acid, the method comprising the steps of:
(a) treating the raw material fat with a lipolytic enzyme;
(b) fractionating the treated substance of the step (a);
(c) ethyl-esterifying a fraction obtained in the step (b) as needed (for example, in the case that the fraction obtained in the step (b) is a fraction that is not ethyl-esterified);
(d) purifying and fractionating the ethyl-esterified glyceride fraction into:
   (1) a fraction comprising more docosahexaenoic acid ethyl ester than the ethyl-esterified glyceride fraction prior to the purifying and comprising less eicosapentaenoic acid ethyl ester than the ethyl-esterified glyceride fraction prior to the purifying; and
   (2) a fraction comprising more eicosapentaenoic acid ethyl ester than the ethyl-esterified glyceride fraction prior to the purifying and comprising less docosahexaenoic acid ethyl ester than the ethyl-esterified glyceride fraction prior to the purifying;
(e) purifying and fractionating the ethyl-esterified free fatty acid fraction into:
   (3) a fraction comprising more docosahexaenoic acid ethyl ester than the ethyl-esterified free fatty acid fraction prior to purification and comprising less eicosapentaenoic acid ethyl ester than the ethyl-esterified free fatty acid fraction prior to purification; and
   (4) a fraction comprising more eicosapentaenoic acid ethyl ester than the ethyl-esterified free fatty acid fraction prior to purification and comprising less docosahexaenoic acid ethyl ester than the ethyl-esterified free fatty acid fraction prior to purification;
(f) mixing the fraction of (1) in the step (d) and the fraction of (3) in the step (e);
(g) mixing the fraction of (2) in the step (d) and the fraction of (4) in the step (e);

(h) further purifying the mixture in the step (f) to obtain a purified substance comprising the docosahexaenoic acid ethyl ester; and
(i) further purifying the mixture in the step (g) to obtain a purified substance comprising the eicosapentaenoic acid ethyl ester.
(Item 2)

A method for preparing an eicosapentaenoic acid ethyl ester and a docosahexaenoic acid ethyl ester from a raw material fat comprising eicosapentaenoic acid and docosahexaenoic acid, the method comprising the steps of:
(a) treating the raw material fat with a lipolytic enzyme under a condition of ethyl-esterifying a fatty acid;
(b) fractionating the treated substance of the step (a) into a glyceride fraction and an ethyl-esterified free fatty acid fraction;
(c) ethyl-esterifying the glyceride fraction obtained in the step (b);
(d) purifying and fractionating the ethyl-esterified glyceride fraction obtained in the step (c) into:
  (1) a fraction comprising more docosahexaenoic acid ethyl ester than the ethyl-esterified substance of the glyceride fraction in the step (c) and comprising less eicosapentaenoic acid ethyl ester than the ethyl-esterified substance of the glyceride fraction in the step (c); and
  (2) a fraction comprising more eicosapentaenoic acid ethyl ester than the ethyl-esterified substance of the glyceride fraction in the step (c) and comprising less docosahexaenoic acid ethyl ester than the ethyl-esterified substance of the glyceride fraction in the step (c);
(e) purifying and fractionating the ethyl-esterified free fatty acid fraction obtained in the step (b) into:
  (3) a fraction comprising more docosahexaenoic acid ethyl ester than the ethyl-esterified free fatty acid fraction in the step (b) and comprising less eicosapentaenoic acid ethyl ester than the ethyl-esterified free fatty acid fraction in the step (b); and
  (4) a fraction comprising more eicosapentaenoic acid ethyl ester than the ethyl-esterified free fatty acid fraction in the step (b) and comprising less docosahexaenoic acid ethyl ester than the ethyl-esterified free fatty acid fraction in the step (b);
(f) mixing the fraction of (1) in the step (d) with the fraction of (3) in the step (e);
(g) mixing the fraction of (2) in the step (d) with the fraction of (4) in the step (e);
(h) further purifying the mixture in the step (f) to obtain a purified substance comprising the docosahexaenoic acid ethyl ester; and
(i) further purifying the mixture in the step (g) to obtain a purified substance comprising the eicosapentaenoic acid ethyl ester.
(Item 3)

A method for preparing an eicosapentaenoic acid ethyl ester and a docosahexaenoic acid ethyl ester from a raw material fat comprising eicosapentaenoic acid and docosahexaenoic acid, the method comprising the steps of:
(a) treating a raw material fat with a lipolytic enzyme;
(b) fractionating the treated substance of the step (a) into a glyceride fraction and a free fatty acid fraction;
(c) ethyl-esterifying each of the glyceride fraction and the free fatty acid fraction obtained in the step (b);
(d) purifying and fractionating the ethyl-esterified glyceride fraction obtained in the step (c) into:
  (1) a fraction comprising more docosahexaenoic acid ethyl ester than an ethyl-esterified substance of the glyceride fraction in the step (c) and comprising less eicosapentaenoic acid ethyl ester than the ethyl-esterified substance of the glyceride fraction in the step (c); and
  (2) a fraction comprising more eicosapentaenoic acid ethyl ester than the ethyl-esterified substance of the glyceride fraction in the step (c) and comprising less docosahexaenoic acid ethyl ester than the ethyl-esterified substance of the glyceride fraction in the step (c);
(e) purifying and fractionating the ethyl-esterified free fatty acid fraction obtained in the step (c) into:
  (3) a fraction comprising more docosahexaenoic acid ethyl ester than the ethyl-esterified substance of the free fatty acid fraction in the step (c) and comprising less eicosapentaenoic acid ethyl ester than the ethyl-esterified substance of the free fatty acid fraction in the step (c);
  (4) a fraction comprising more eicosapentaenoic acid ethyl ester than the ethyl-esterified substance of the free fatty acid fraction in the step (c) and comprising less docosahexaenoic acid ethyl ester than the ethyl-esterified substance of the free fatty acid fraction in the step (c);
(f) mixing the fraction of (1) in the step (d) and the fraction of (3) in the step (e);
(g) mixing the fraction of (2) in the step (d) and the fraction of (4) in the step (e);
(h) further purifying the mixture in the step (f) to obtain a purified substance comprising the docosahexaenoic acid ethyl ester; and
(i) further purifying the mixture in the step (g) to obtain a purified substance comprising the eicosapentaenoic acid ethyl ester.
(Item 4)

The method according to any one of Items 1 to 3, wherein the raw material fat is a deacidified raw material fat.
(Item 5)

The method according to Item 4, wherein an acid value of the deacidified raw material fat is 3 or less.
(Item 6)

The method according to any one of Items 1 to 3, wherein the raw material fat comprising 4 wt % or more eicosapentaenoic acid and 4 wt % or more docosahexaenoic acid.
(Item 7)

The method according to any one of Items 1 to 3, wherein the lipolytic enzyme is a microorganism-derived lipase that selectively hydrolyzes positions 1 and 3 of triglyceride.
(Item 8)

The method according to any one of Items 1 to 3, wherein the fractionating in the step (b) is performed using a method selected from the group consisting of a falling thin-film molecular distillation method, a centrifugal molecular distillation method and an elution method.
(Item 9)

The method according to Item 8, wherein: the fractionating in the step (b) is performed using the elution method; an eluate obtained by using hexane is recovered as an ethyl-esterified free fatty acid fraction; and an eluate obtained by using diethyl ether is recovered as the glyceride fraction.
(Item 10)

The method according to any one of Items 1 to 3, wherein the ethyl-esterifying of the glyceride fraction in the step (c) is performed using an alkali catalyst method or an enzymic method.

(Item 11)

The method according to any one of Items 1 to 3, wherein the ethyl-esterifying of the free fatty acid fraction in the step (c) is performed using an acid catalyst method or an enzymic method.

(Item 12)

The method according to any one of Items 1 to 3, wherein the purifying in the step (d) is performed using a method selected from the group consisting of a vacuum precision distillation method, a urea addition method, a silver nitrate complex method, a fixed-bed chromatography method and an SMB chromatography method.

(Item 13)

The method according to any one of Items 1 to 3, wherein the purifying in the step (e) is performed using a method selected from the group consisting of a vacuum precision distillation method, a urea addition method, a silver nitrate complex method, a fixed-bed chromatography method and an SMB chromatography method.

(Item 14)

The method according to any one of Items 1 to 3, wherein the purifying in the step (h) is performed using a method selected from the group consisting of a vacuum precision distillation method, a urea addition method, a silver nitrate complex method, a fixed-bed chromatography method and an SMB chromatography method.

(Item 15)

The method according to any one of Items 1 to 3, wherein the purifying in the step (i) is performed using a method selected from the group consisting of a vacuum precision distillation method, a urea addition method, a silver nitrate complex method, a fixed-bed chromatography method and an SMB chromatography method.

(Item 16)

The method according to any one of Items 1 to 3, wherein:
concentration of the docosahexaenoic acid ethyl ester of the fraction (1) in the step (d) is 15 wt % or more;
concentration of the eicosapentaenoic acid ethyl ester of the fraction (2) in the step (d) is 15 wt % or more;
concentration of the docosahexaenoic acid ethyl ester of the fraction (3) in the step (e) is 15 wt % or more; and
concentration of the eicosapentaenoic acid ethyl ester of the fraction (4) in the step (e) is 15 wt % or more.

(Item 17)

The method according to any one of Items 1 to 3, wherein:
concentration of the docosahexaenoic acid ethyl ester is 15 wt % or more and concentration of the eicosapentaenoic acid ethyl ester is 15 wt % or less in the mixture in the step (f); and
concentration of the eicosapentaenoic acid ethyl ester is 15 wt % or more and concentration of the docosahexaenoic acid ethyl ester is 15 wt % or less in the mixture in the step (g).

(Item 18)

The method according to any one of Items 1 to 3, wherein:
concentration of the docosahexaenoic acid ethyl ester in the purified substance in the step (h) is 70 wt % or more; and
concentration of the eicosapentaenoic acid ethyl ester in the purified substance in the step (i) is 70 wt % or more.

(Item 19)

The method according to any one of Items 1 to 3, further comprising the following steps of:
(j) treating the purified substance obtained in the step (h) with an adsorbent to remove impurities; and
(k) treating the purified substance obtained in the step (i) with an adsorbent to remove impurities.

(Item 20)

The method according to Item 19, wherein: the adsorbent is selected from the group consisting of acid white earth, activated white earth, activated charcoal, silicic acid and alumina; and a peroxide value after the adsorbent treatment is 3 or less.

(Item 21)

The method according to Item 19, further comprising the following steps of:
(l) adding an antioxidant agent to the substance obtained in the step (j); and
(m) adding an antioxidant agent to the substance obtained in the step (k).

(Item 22)

The method according to Item 21, wherein the antioxidant agent is selected from the group consisting of tocophenol, ascorbyl palmitate, catechin and a rosemary extract.

Effect of the Invention

The present invention provides a method for obtaining a ω3 fatty acid ethyl ester such as EPA and DHA each as a high purity product at a high yield. The present invention makes it possible to provide a less expensive and high purity ω3 fatty acid ethyl ester such as EPA and DHA.

EMBODIMENTS FOR CARRYING OUT THE INVENTION

Hereinafter, the present invention will be described. Throughout the present specification, unless specifically referred to, an expression in a singular form is to be understood to encompass the concept of its plurality form. Furthermore, terms used herein, unless specifically referred to, are to be understood to be used in the meaning usually used in the art. Therefore, unless defined otherwise, all technical terms and scientific terms herein have the same meaning as generally recognized by those skilled in the art. In case of contradiction, the present specification (including the definition) governs. In addition, "wt %" herein is interchangeably used with "percent-by-mass concentration".

Definition of Terms

Hereinafter, definitions of terms particularly used herein will be listed.

The term, "raw material fat", as used herein refers to fat used as a raw material for the purification according to the present invention. The raw material fat may or may not be deacidified. Preferably, the raw material fat according to the present invention is a deacidified raw material fat.

The term, "glyceride", as used herein refers to includes components selected from the group consisting of triglyceride, diglyceride and monoglyceride of fatty acids. According to the present invention, unless defined otherwise, the "glyceride" does not include phospholipid or glycolipid.

The term, "lipolytic enzyme", as used herein refers to an enzyme that degrades a lipid, and typically refers to lipase. Preferably, the "lipolytic enzyme" according to the present invention is a lipase, and more preferably a lipase which selectively hydrolyzes positions 1 and 3 of triglyceride. The "lipolytic enzyme" as used herein may be a natural enzyme or a recombinant enzyme. In addition, the "lipolytic enzyme" as used herein may be in the form of a solution or in an immobilized form.

The term, "glyceride fraction", as used herein refers to a fraction which includes a relatively large amount of glyceride among mixed fat fractions in a reaction solution obtained after a raw material fat is treated with a lipolytic enzyme, e.g., fraction with a higher ratio of the glyceride to free fat acids compared to other fractions. The fatty acid in a glycerin fatty acid ester included in a glyceride fraction may or may not be ethyl-esterified.

The term, "free fatty acid fraction" as used herein refers to a fraction which includes a relatively large amount of free fat acid among mixed fat fractions in a reaction solution obtained after a raw material fat is treated with a lipolytic enzyme, e.g., fraction with a higher ratio of the free fatty acid to glyceride compared to other fractions. The free fatty acid of the free fatty acid fraction may or may not be ethyl-esterified.

The term, "ethyl-esterification", as used herein refers to a reaction of esterifying glyceride and/or a fatty acid in the presence of ethyl alcohol. Methods for esterifying glyceride are well known in the subject field. Methods for esterifying a fatty acid are well known in the subject field. For example, if a raw material fat is treated with a lipolytic enzyme in the presence of ethyl alcohol, then the resulting free fat acid fraction is an ethyl-esterified free fat acid.

The term, step of "ethyl-esterifying a fraction", as used herein refers to a step of ethyl-esterifying at least one of substances included in a fraction.

The term, step of "ethyl-esterifying a glyceride fraction", as used herein refers to a step of ethyl-esterifying a component in a glyceride fraction (preferably, ethyl-esterifying a fatty acid portion of a glycerin fatty acid ester included in the glyceride fraction).

The term, "ethyl-esterified glyceride fraction", as used herein refers to a fraction in which a substance included in a glyceride fraction is ethyl-esterified (preferably, a fatty acid portion of a glycerin fatty acid ester included in the glyceride fraction is ethyl-esterified).

The term, step of "ethyl-esterifying a free fatty acid fraction", as used herein refers to a step of ethyl-esterifying a free fatty acid fraction (preferably, a free fatty acid in the free fatty acid fraction).

The term, "ethyl-esterified free fat acid fraction", as used herein refers to a fraction in which a substance included in a free fat acid fraction (preferably, a free fatty acid in the free fat acid fraction) is ethyl-esterified.

The term, "docosahexaenoic acid", as used herein is interchangeably used with "DHA" and encompasses both a form of a free fatty acid and a form that is ester-bonded with glycerin.

The term, "docosahexaenoic acid ethyl ester", as used herein is interchangeably used with "DHA ethyl ester" and encompasses both a form of an ethyl-esterified free fatty acid and a form of an ethyl-esterified docosahexaenoic acid ester-bound to glycerin.

The term, "eicosapentaenoic acid", as used herein is interchangeably used with "EPA" and encompasses both a form of a free fatty acid and a form that is ester-bonded with glycerin.

The term, "eicosapentaenoic acid ethyl ester", as used herein is interchangeably used with "EPA ethyl ester" and encompasses both a form of an ethyl-esterified free fatty acid and ethyl-esterified eicosapentaenoic acid ester-bonded with glycerin.

The term, "purification", as used herein refers to any operation of increasing a concentration of a substance targeted for purification.

The term, "SMB chromatography", as used herein refers to a separation method utilizing the principle of liquid chromatography, which is chromatography using a moving bed, in which a plurality of unit packed beds filled with an adsorbent having different selective adsorption capabilities to a specific component and another specific component in a raw material filled therein are connected in series and in which the unit packed bed in the downmost-stream part is connected with the packed bed in the uppermost-stream part, thereby forming an endless circulating system. Herein, the "SMB chromatography" is interchangeably used with "simulated moving bed chromatography".

(Purification Method According to the Present Invention)

The present invention provides a method that encompasses: a method for preparing a high purity ω3 fatty acid ethyl ester (for example, without limitation, an EPA ethyl ester and a DHA ethyl ester are included), comprising:

(a) treating the raw material fat with a lipolytic enzyme (Due to the subject step, a DHA-rich glyceride fraction and an EPA-rich free fatty acid fraction are produced. In accordance with the reaction conditions, the free fatty acid may be an ethyl-esterified free fatty acid or may be a free fatty acid that is not ethyl-esterified);

(b) fractionating the treated substance of the step (a) into a glyceride fraction and a free fatty acid fraction (the free fatty acid may be either an ethyl-esterified free fatty acid or a free fatty acid that is not ethyl-esterified);

(c) ethyl-esterifying a fraction obtained in the step (b) as needed (for example, in the case that the glyceride and/or free fatty acid is not ethyl-esterified);

(d) purifying and fractionating the ethyl-esterified glyceride fraction into:
 (1) a fraction comprising more docosahexaenoic acid ethyl ester than the ethyl-esterified substance of the raw material glyceride fraction (ethyl-esterified substance of the glyceride fraction in the step (b) or (c)) and comprising less eicosapentaenoic acid ethyl ester than the ethyl-esterified substance of the raw material glyceride fraction (ethyl-esterified substance of the glyceride fraction in the step (b) or (c)); and
 (2) a fraction comprising more eicosapentaenoic acid ethyl ester than the ethyl-esterified substance of the raw material glyceride fraction (ethyl-esterified substance of the glyceride fraction in the step (b) or (c)) and comprising less docosahexaenoic acid ethyl ester than the ethyl-esterified substance of the raw material glyceride fraction (ethyl-esterified substance of the glyceride fraction in the step (b) or (c));

(e) purifying and fractionating the ethyl-esterified free fatty acid fraction into:
 (3) a fraction comprising more docosahexaenoic acid ethyl ester than the ethyl-esterified substance of the raw material free fatty acid fraction (ethyl-esterified substance of the free fatty acid fraction in the step (b) or (c)) and comprising less eicosapentaenoic acid ethyl ester than the ethyl-esterified substance of the raw material free fatty acid fraction (ethyl-esterified substance of the free fatty acid fraction in the step (b) or (c)); and
 (4) a fraction comprising more eicosapentaenoic acid ethyl ester than the ethyl-esterified substance of the raw material free fatty acid fraction (ethyl-esterified substance of the free fatty acid fraction in the step (b) or (c)) and comprising less docosahexaenoic acid ethyl ester than the ethyl-esterified substance of the raw material free fatty acid fraction (ethyl-esterified substance of the free fatty acid fraction in the step (b) or (c));

(f) mixing the fraction of (1) in the step (d) and the fraction of (3) in the step (e);

(g) mixing the fraction of (2) in the step (d) and the fraction of (4) in the step (e);

(h) further purifying the mixture in the step (f) to obtain a purified substance comprising the docosahexaenoic acid ethyl ester (note that a fraction comprising more eicosapentaenoic acid ethyl ester obtained in the purifying step can also be used as an eicosapentaenoic acid ethyl ester purified substance); and (i) further purifying the mixture in the step (g) to obtain a purified substance comprising the eicosapentaenoic acid ethyl ester (note that a fraction comprising more docosahexaenoic acid ethyl ester obtained in the purifying step can also be used as a docosahexaenoic acid ethyl ester purified substance).

(1. Raw Material Fat)

The raw material fat used in the above-mentioned step (a) preferably comprises 4 wt % or more eicosapentaenoic acid and 4 wt % or more docosahexaenoic acid. For example, the raw material fat used in the present invention includes, without limitation, fat of marine products (hereinafter, referred to as "marine fat"). The marine fat includes, without limitation, anchovy oil, pilchard oil, sardine oil, menhaden oil, salmon oil, herring oil, bonito oil, tuna oil as well as marine algae-derived fat. The fish oil names as used herein conform to Gyokairui no shibousan soseihyou, Japan Aquatic Oil Assoc., Korin (Tokyo), 1989.

The purity of EPA included in marine fat used as a raw material in the present invention is, without limitation, preferably 4.0 wt % or more and 60 wt % or less, and more preferably 10 wt % or more and 60 wt % or less. In addition, the purity of DHA included in marine fat used in the present invention is, without limitation, preferably 4.0 wt % or more and 60 wt % or less, and more preferably 10 wt % or more and 35 wt % or less. In the case that the raw material used in the present invention contains only EPA in the above-mentioned concentration range and also contains DHA at or less than the above-mentioned concentration, such raw material fat can be used as a starting material for purifying high purity EPA. In the case that the raw material fat used in the present invention contains only DHA in the above-mentioned concentration range and also contains EPA at or less than the above-mentioned concentration, such raw material fat can be used as a starting material for purifying high purity DHA.

The raw material fat used in the above-mentioned step (a) is preferably deacidified fat. Methods for deacidification treatment are well known, and Non-Patent Document 1 (Kosaku YASUDA et al., Yushiseihin no chishiki, Saiwai Shobou (Tokyo), 1977, pp. 103-104), for example, describes such a method. The acid value of the deacidified raw material fat (hereinafter, referred to as "AV") is, without limitation, 3.0 or less, and preferably 1.0 or less. Normally, 90 wt % or more of the raw material fat is glyceride of fatty acids, and furthermore, 90 wt % or more thereof is triglyceride, and the remaining glyceride is diglyceride and monoglyceride. The concentration of the glyceride of fatty acids in the raw material fat varies in accordance with the derivation of the raw material fat, which does not restrict the present invention.

The method for analyzing a fatty acid composition, acid value, and a method for measuring a peroxide value (hereinafter, referred to as "POV") as used herein are well known, and they are as described in, for example, 2003 Nenban Kijun Yushi Bunseki Shikenhou (Japan Oil Chemists' Society).

The raw material fat used in the above-mentioned step (a) is preferably degummed fat. Methods of degumming treatment are well known and are described, for example, in Non-Patent Document 1 (Kosaku YASUDA et al., Yushiseihin no chishiki, Saiwai Shobou (Tokyo), 1977, pp. 103-104). Although degumming treatment is not mandatory, raw material fat that has undergone degumming treatment contains fewer impurities, which allows the following purifying step to be facilitated.

(2. Lipolytic Enzyme Treatment)

Raw material fat (typically, raw material fat after deacidification treatment) is treated with a lipolytic enzyme. EPA and DHA included in raw material fish oil are normally considered as having a high percentage of being bound to position 2 of glyceride (Mitsumasa MANKURA and Mitsu KAYAMA, AA, EPA, DHA no seirikinou to riyou, "AA, EPA, DHA-Koudo fuhouwa shibousan", Mitsu KAYAMA, Kouseisha-kouseikaku Corp. (Tokyo), 1995, pp. 207-224). Accordingly, it is preferable to use a lipolytic enzyme (lipase) having position 1 selectivity and/or position 3 selectivity in the present invention. Lipolytic enzymes (lipase) derived from microorganisms include, for example, without limitation, *Candida cylindoracea*-derived lipase OF (trade name, Meito Sangyo Co., Ltd.), *Alcaligenes* sp.-derived lipase QLM, lipase QLC, and lipase PL (which are all trade names, Meito Sangyo Co., Ltd.), *Burkholderia cepacia*-derived lipase PS (trade name, Amano Enzyme Inc.), *Pseudomonas fluorescens*-derived lipase AK (trade name, Amano Enzyme Inc.) and the like. Preferably, the lipolytic enzyme (lipase) used in the present invention is a lipase derived from microorganisms that selectively hydrolyzes positions 1 and 3 of triglyceride. According to the present invention, immobilized lipase, e.g., immobilized lipase derived from *Thermomyces lanuginosa*, Lipozyme TLIM (trade name, Novozymes), can be used without limitation thereto. These lipases have high position 1 or 3 selectivity. Thus, EPA and DHA mainly bound to position 2 remain as glyceride to be a glyceride fraction, and the remaining fatty acids bound to positions 1 or 3 remain within the system as a free fatty acid fraction.

With regard to the treatment with lipolytic enzyme, there is no restriction on reaction time, temperature or the like. Those skilled in the art are able to use well-known conditions described in, for example, Patent Documents 1 to 3. The progress of enzymatic reactions can be managed through AV measurement. While the AV with which a reaction should be stopped can be freely set in accordance with the quality of targeted products, such as the type of starting material, EPA purity and DHA purity, the reaction is generally stopped in the range from 30 to 130, and desirably in the range from 70 to 100. For example, if lipolytic enzyme treatment is performed in the presence of ethyl alcohol, glyceride in fatty acids is degraded into fatty acids and glyceride and free fatty acids are ethyl-esterified.

(3. Fractionating to a Glyceride Fraction and a Free Fatty Acid Fraction)

A reaction solution after the completion of lipolytic enzyme (lipase) treatment can be separated into a mixed fat fraction, including a glyceride fraction and a free fatty acid fraction (wherein the fatty acid in the fatty acid fraction may or may not be ethyl-esterified), and an aqueous fraction. This separation can be performed using a well-known method such as a two-layer liquid-liquid separation method or a centrifugation method. Water, enzyme-derived impurities and the like are removed from the reaction solution using such a method to obtain a liquid mixture of a glyceride fraction and a free fatty acid fraction.

Next, the liquid mixture comprising a glyceride fraction and a free fatty acid fraction is separated into a glyceride fraction and a free fatty acid fraction. This separation can be performed using a centrifugal molecular distillation method, a falling thin film molecular distillation method or an elution method. For example, in the case of the falling film molecular distillation method, as described in Japanese Laid-Open Publication No. 2000-342291, treatment can be performed under the conditions of 0.005 mmHg degree of vacuum, 200° C. evaporation front temperature and 30 g/L flow rate, and a free fatty acid fraction can be obtained as a fraction and a glyceride fraction can be obtained as a residue. In the case of the falling film molecular distillation method, those skilled in the art can appropriately change the degree of vacuum, evaporation front temperature and/or feed amount in molecular distillation operations in accordance with the model of apparatuses and the difference in raw material fat. In the case of the elution method, typically, for example, an eluate obtained by using hexane is recovered as an ethyl-esterified free fatty acid fraction, and an eluate obtained by using diethyl ether is recovered as a glyceride fraction. Those skilled in the art can appropriately select a combination of these solvents.

(4. Ethyl-Esterification)

As described above, the free fatty acid may or may not be ethyl-esterified as a result of an enzymic reaction depending on the reaction conditions of the lipolytic enzyme. If the glyceride fraction (in particular, the fatty acid portion of the glycerin fatty acid ester included in the glyceride fraction) and/or free fatty acid fraction (in particular, the free fatty acid in the free fatty acid fraction) are not ethyl-esterified, ethyl-esterification is performed thereon.

Ethyl-esterification methods of a fraction including a fatty acid are well known. For example, the fatty acid in the fractionated glyceride fraction is ethyl-esterified by an acid catalyst, an alkali catalyst or enzyme (lipase) in the coexistence of ethyl alcohol. Preferably, the fatty acid in a glycerin fatty acid ester included in the fractionated glyceride fraction is ethyl-esterified using an alkali catalyst method or an enzymic method. The fatty acid in the fractionated free fatty acid fraction is ethyl-esterified by an acid catalyst or enzyme (lipase) in the coexistence of ethyl alcohol (Non-Patent Document 2, Patent Document 4). When enzyme is used, the amount of ethyl alcohol to be added is preferably an amount that will not deactivate the enzyme, which is preferably 4 molar equivalent or less, and still preferably 2 molar equivalent or less with respect to the glyceride or free fatty acid, without limitation thereto. In general, the glyceride fraction includes DHA ethyl ester more than EPA ethyl ester, while the free fatty acid fraction includes EPA ethyl ester more than DHA ethyl ester.

The ethyl-esterifying step does not necessarily have to be performed separately from the above-mentioned lipolytic enzyme treatment. For example, if treatment of raw material fat is performed with a lipolytic enzyme such as lipase under the ethyl-esterification condition (e.g., lipase treatment in the presence of ethyl alcohol), ethyl-esterification can be performed simultaneously with lipid degradation. If the treatment of raw material fat with a lipolytic enzyme is performed simultaneously with ethyl-esterification, ethyl-esterification does not have to be performed again after the enzymic treatment. For example, if the treatment of raw material fat with a lipolytic enzyme is performed simultaneously with ethyl-esterification, fractionation can be made into an ethyl ester fraction and a residue (glyceride fraction) after the enzymic treatment.

(5. Purification of Ethyl-Esterified Glyceride Fraction and/or Free Fatty Acid Fraction)

As to the purification of an ethyl-esterified glyceride fraction and/or a free fatty acid fraction, for example, purification methods includes, without limitation, a vacuum precision distillation method, a urea addition method, a silver nitrate complex method, a chromatography method and the like. These purification methods are well known. The outlines of the methods will be described hereinafter.

(5.1. Vacuum Precision Distillation Method)

The vacuum precision distillation method is a method for separation using the difference in boiling points of respective components. In the case of EPA, the component whose number of carbon chain including EPA is 20 is positioned at an intermediate boiling point among fish oil fatty acids. A single tower distillation apparatus needs to be used in the case of batch types, while a twin tower or four tower apparatus needs to be used in the case of continuous distillation. In the case of the twin tower type, components of C19 or less (initial distillation) are distilled, and the residual is sent to the second tower and C20 components (main distillation) are recovered, thereby performing purification.

(5.2. Urea Addition Method)

The urea addition method is a purification method which utilizes characteristics of dissolved urea forming a hexagonal additive crystal while incorporating linear chain molecules when the urea is crystallized. For example, a raw material and a urea methanol solution are mixed and cooled down to form a urea additive in which saturated fatty acid and mono-unsaturated fatty acid are incorporated, followed by filtration to perform purification. Typically, n-hexane extraction is performed from an urea additive, followed by silica gel treatment, and then n-hexane is distilled away to obtain a target unsaturated fatty acid.

(5.3. Silver Nitrate Complex Method)

The silver nitrate complex method is a purification method which utilizes characteristics of a silver nitrate solution forming a complex with respect to double bond of fatty acids. In the case of purifying highly-unsaturated fatty acid ethyl ester, a raw material and a silver nitrate solution are stirred and n-hexane extraction, for example, is performed on unreacted ester. Thereafter, the aqueous phase is diluted or warmed, and free ester is extracted again with n-hexane to perform concentration and purification of a target highly-unsaturated fatty acid ethyl ester.

(5.4. Chromatography Method)

The chromatography method includes a method using a fixed bed (fixed-bed chromatography method) and an SMB chromatography method (simulated moving bed chromatography method). The fixed-bed chromatography method is a method in which a filler is put in a column, and a raw material is allowed to pass it through with an eluant to extract a fraction that includes a target component, followed by concentration and purification. In the method according to the present invention, preferable fillers include, without limitation, silica gel, reverse-phase silica gel, and silver nitrate-containing silica gel.

(5.5. Typical Purification Methods)

Purification of fatty acid ethyl ester from an ethyl-esterified glyceride fraction can be performed using, for example, a vacuum precision distillation method, a urea addition method, a silver nitrate complex method, a chromatography method and the like (Patent Documents 4 to 9). (1) Using any of these methods, it becomes possible to obtain an EPA ethyl ester fraction with 15 wt % or more concentration (preferably, 50 wt % or more, and more preferably 80 wt % or more concentration) and a DHA ethyl ester fraction with 15 wt % or more concentration (preferably 20 wt % or more, and more preferably 35 wt % or more concentration) from an ethyl-esterified glyceride fraction. (2) Purification of a fatty acid ethyl ester from an ethyl-esterified free fatty acid fraction can be performed using, for example, a vacuum precision distillation method, a urea addition method, a silver nitrate complex method, a chromatography method and the like (Patent Documents 4 to 9). Using any of these methods, it becomes possible to obtain an EPA ethyl ester fraction with 15 wt % or more concentration and a DHA ethyl ester fraction with 10 wt % or more concentration (preferably, 15 wt % or more concentration) from an ethyl-esterified free fatty acid fraction.

Subsequently, a fraction rich in EPA ethyl esters from an ethyl-esterified substance of the glyceride fraction is put together with a fraction rich in EPA ethyl esters from an ethyl-esterified substance of the free fatty acid fraction to prepare an EPA ethyl ester fraction (preferably, with 15 wt % or more purity); and a fraction rich in DHA ethyl esters from the glyceride fraction is put together with a fraction rich in DHA ethyl esters from the free fatty acid fraction to prepare a DHA ethyl ester fraction (preferably, with 15 wt % or more purity).

Subsequently, each of the EPA ethyl ester fraction and DHA ethyl ester fraction obtained by the mixture of the fractions described above is concentrated and purified again using a vacuum precision distillation method, a urea addition method, a silver nitrate complex method, a chromatography method or the like.

For example, purification of an EPA ethyl ester fraction with 30 wt % or more purity using a thin-film vacuum precision distillation method in combination with an HPLC method makes it possible to obtain an EPA ethyl ester with 70 wt % or more purity and preferably 95 wt % or more purity at a high yield. The remaining DHA ethyl ester can be used together with the DHA ethyl ester fraction.

In addition, purification of a DHA ethyl ester fraction with 30 wt % or more purity using a thin-film vacuum precision distillation method in combination with an HPLC method makes it possible to obtain a DHA ethyl ester with 70 wt % or more purity and preferably 85 wt % or more purity at a high yield. The remaining EPA ethyl ester can be used together with the EPA ethyl ester fraction.

As such, the concentrated and purified EPA ethyl ester and DHA ethyl ester comprise impurities, such as peroxides of lipid produced during purification, colored substances and foreign substances derived from raw material. Thus, adsorbent treatment is performed using a combination of one or more adsorbents selected from activated white earth, acid white earth, silicic acid, silica gel, alumina and the like based on publicly known methods (Patent Documents 10 to 12), so that, for example, the POV can be 3 or less, desirable 1 or less (i.e., removal of impurities including peroxides of lipid makes it possible to reduce the POV).

The resulting high-purity EPA ethyl ester and high-purity DHA ethyl ester may be blended with a substance selected from the group consisting of tocophenol, ascorbyl palmitate, catechin and a rosemary extract, as an antioxidant agent for the quality preservation.

(6. SMB Chromatography)

In SMB chromatography, a raw material and an eluent are supplied to an endless circulating system, and an X component (i.e., weak-affinity component) moving at a fast rate within a column (unit packed bed) and a Y component (i.e., affinity component) moving at a slow rate within a column are respectively extracted from different positions. Furthermore, in the SMB chromatography, a raw material supplying position, an eluent supplying position, an X component extracting position and a Y component extracting position are sequentially moved towards the downstream side in the fluid circulating direction while maintaining a constant positional relationship thereof, so that treatment operations for continuously performing raw material supply can be artificially achieved. As a result, the operation method is such that the distribution state of the respective components in the bed moves with a substantially constant width and the extracting positions of the respective components can continue to take a portion high in both purity and concentration.

In the SMB chromatography according to the present invention, one type of columns may be used, or two or more types of columns may be used. For example, according to the present invention, C18 columns only may be used (e.g., four C18 columns), or three C18 columns and one C8 column (or C4 columns or C1 columns instead of the C8 columns) may be used. The column size is not limited, but columns of, for example, 10 mm in diameter×500 mm in height may be used. Those skilled in the art can appropriately determine conditions of the chromatography. For example, as for the conditions of chromatography, without limitation, the amount of raw material fat supplied is determined to be 21 mL per hour per 1 L filler (21 mL/L-R/h), and an eluent (e.g., methanol) is used at the eluent amount: 400 mL per hour per 1 L filler (0.40 L/L-R/h).

Hereinafter, the present invention will be described in detail through Examples or the like, but it should be understood that the present invention is not limited to such Examples.

EXAMPLES

Example 1

With 100.0 kg Peruvian anchovy oil (AV2.5, SDA 0.7 wt %, EPA 17.5 wt %, DHA 9.2 wt %) as a starting raw material, alkali deacidification treatment was performed in accordance with conventional methods, thus obtaining 95.0 kg deacidified anchovy oil with AV 0.5 (SDA indicates all-cis-6, 9, 12, 15-octadecatrienoic acid, and is also referred to as "18:4ω3"). 100 liter water and 2,000 unit/g lipase OF (Meito Sangyo Co., Ltd.) were added to the resulting anchovy oil, and the mixture was stirred at 40° C. and the enzymic reaction was allowed to continue. When the AV reached 85 (about 12 hour reaction), the reaction was stopped, and moisture was removed by centrifugation. Thereafter, the oil layer was washed three times with about 30 liters of water in order to remove impurities such as glycerin, thus obtaining a 94.5 kg mixed oil including the glyceride fraction and free fatty acid fraction. The mixed oil was treated with a 0.005 mmHg degree of vacuum and the 200° C. evaporation front temperature using a falling thin-film molecular distillation apparatus, thus obtaining a 44 kg free fatty acid fraction (SDA 0.8 wt %, EPA 16.2 wt %, DHA 5.5 wt %) on the fraction side and 50 kg fatty acid glyceride (SDA 0.6%, EPA 19.0%, DHA 12.9%) on the residue side.

According to conventional methods, the free fatty acid fraction was ethyl-esterified using an acid catalyst method, thus obtaining a 46.5 kg product. The glyceride fraction was ethyl-esterified using an alkali catalyst method, thus obtaining a 49.0 kg product.

With regard to both of the ethyl ester obtained from the glyceride fraction and the ethyl ester obtained from the free fatty acid fraction, they were separated and purified using a vacuum precision distillation method in reference to Cited Reference 9, thus obtaining the products in Table 1.

TABLE 1

Primary fatty acid composition of vacuum precision distillation fraction products (wt %)

| | fraction | | | |
|---|---|---|---|---|
| | Glyceride fraction | | Free fatty acid fraction (FFA) | |
| Fatty acid composition | (1) DHA-EE fraction | (2) EPA-EE fraction | (3) DHA-EE fraction | (4) EPA-EE fraction |
| SDA-EE (wt %) | 0.4 | 1.8 | 0.5 | 2.4 |
| EPA-EE (wt %) | 3.7 | 66.1 | 3.1 | 78.4 |
| DHA-EE (wt %) | 60.3 | 2.2 | 55.9 | 2.3 |
| Recovered weight (Kg) | 8.1 | 12.2 | 4.1 | 8.9 |

From the respective fraction products, 12.2 kg DHA ethyl ester (DHA-EE) fraction (SDA 0.5%, EPA 3.5%, DHA 58.9%) obtained by mixing (1) and (3) and 21.1 kg EPA ethyl ester (SDA 2.1%, EPA 71.5%, DHA 8.1%) obtained by mixing (2) and (4) were prepared.

The DHA ethyl ester fraction and the EPA ethyl ester fraction were respectively treated using simulated moving bed chromatography (SMB). Reversed phase (ODS) columns (four C18 columns were used) were attached and methanol was used for an eluent.

As a result, 6.8 kg of 95.2 wt % DHA ethyl ester (70.2% DHA yield, POV 3.8) was recovered from the DHA ethyl ester fraction, and 13.6 kg of 96.5 wt % EPA ethyl ester (75.0% EPA yield, POV 3.3) was recovered from the EPA ethyl ester fraction.

1.0 wt % activated white earth was added to each of the DHA ethyl ester and EPA ethyl ester described above, and each ester was stirred at 40° C. for an hour under reduced pressure, and thereafter, a preparation was obtained through suction filtration in the presence of nitrogen gas. The yield at this time was 99.0 wt % (POV 0.5) for both.

0.2 wt % DL-α-tocopherol was added to these purified preparations, followed by mixing and dissolving under nitrogen gas flow, thus obtaining a product.

Comparative Example 1

In order to demonstrate effects of enzymic treatment in Example 1, purification was performed using the same method as in Example 1, except for not including an enzymatic treatment step. It should be noted that the concentration and purification of EPA ethyl ester were tracked and DHA ethyl ester was not included in order to explicitly show the comparison.

With 100.0 kg Peruvian anchovy oil (AV2.5, SDA 0.7 wt %, EPA 17.5 wt %, DHA 9.2 wt %) as a starting raw material, alkali deacidification treatment was performed in accordance with conventional methods, thereby obtaining 95.0 kg deacidified anchovy oil with AV 0.5.

The deacidified preparation was ethyl-esterified similar to Example 1, and then the ethyl ester was separated and purified through vacuum precision distillation similar to Patent Document 9 and Example 1, thus obtaining an intermediate purified product of EPA ethyl ester. The intermediate purified product was further concentrated and purified using SMB similar to Example 1, obtaining the results shown in Table 2.

TABLE 2

Primary fatty acid compositions in purification processes (wt %)

| | Fraction | | |
|---|---|---|---|
| Fatty acid composition | Prior to vacuum precision distillation† | EPA-EE fraction after vacuum precision distillation | EPA-EE fraction after chromatography purification |
| SDA-EE (wt %) | 0.7 | 3.8 | 3.1 |
| EPA-EE (wt %) | 17.5 | 61.1 | 90.9 |
| DHA-EE (wt %) | 9.2 | 15.7 | 6.3 |
| Recovery weight (Kg) | 95 | 17.4 | 10.8 |
| EPA yield | 95 | 60.8 | 56.1 |

From the results described above, the effectiveness of reducing the ratio of SDA and DHA, which are factors for decreasing the purity of purification, with respect to EPA was demonstrated in concentration and purification steps, such as a vacuum precision distillation step and a chromatography step, and at the same time the importance of adding an enzymic treatment step was demonstrated to this end.

Example 2

In order to observe the effectiveness of enzymic treatment as to raw material fat different from the raw material fat used in Example 1, experiments of Example 2 and Comparative Example 2 were performed. In order to explicitly show the comparison, concentration and purification of EPA ethyl ester were tracked and DHA ethyl ester was not included.

In Example 2, treatment including an enzymic treatment step completely the same as Example 1 was performed, as will be described below. Specifically, 100.0 kg U.S. menhaden oil (AV 4.8, SDA 2.8 wt %, EPA 11.0 wt %, DHA 9.1 wt %) was used as raw material fat. Alkali deacidification treatment was performed on the menhaden oil in accordance with conventional methods, thus obtaining 94.0 kg deacidified menhaden oil of AV 0.5. As a result of performing the same purification as the purification in Example 1, the composition of the EPA ethyl ester fraction prior to vacuum precision distillation was DA-EE 1.2 wt %, EPA-EE wt 52.9%, DHA 15.5 wt %, but 4.8 kg of 95.5 wt % EPA ethyl ester was recovered after the final chromatography purification (EPA yield 41.4%, POV 3.3).

Comparative Example 2

In order to demonstrate the effects of enzymic treatment in Example 2, an experiment of Comparative Example 2 was performed, where the same experiment as that of Example 2 was performed except for not including an enzymic treatment step.

Similar to Example 2, 100.0 kg U.S. menhaden oil (AV 4.8, SDA 2.8 wt %, EPA 11.0 wt %, DHA 9.1 wt %) was used as a starting raw material, and alkali deacidification treatment was performed on the menhaden oil in accordance with conventional methods, thus obtaining 94.0 kg deacidified menhaden oil of AV 0.5.

The deacidified preparation was ethyl-esterified similar to Comparative Example 1, and then the ethyl ester was separated and purified through vacuum precision distillation similar to Patent Document 9 and Comparative Example 1, thus obtaining an intermediate purified product of EPA ethyl ester. The intermediate purified product was further concentrated and purified using a chromatography method (SMB chromatography), obtaining the results shown in Table 3. 3.6 kg of 92.9 wt % EPA ethyl ester was recovered after the final chromatography purification (EPA yield 30.4%, POV 3.3).

TABLE 3

Primary fatty acid compositions in purification processes (wt %)

| | fraction | | |
|---|---|---|---|
| Fatty acid composition | Prior to vacuum precision distillation | EPA-EE fraction after vacuum precision distillation | EPA-EE fraction after chromatography purification |
| SDA-EE (wt %) | 2.8 | 4.1 | 3.7 |
| EPA-EE (wt %) | 11.0 | 55.5 | 92.9 |
| DHA-EE (wt %) | 9.1 | 8.7 | 5.1 |
| Recovery weight (Kg) | 93 | 11.4 | 3.6 |
| EPA yield | 93 | 57.5 | 30.4 |

From the results described above, the effectiveness of reducing the ratio of SDA and DHA, which are factors for decreasing the purity of purification, with respect to EPA was demonstrated in concentration and purification steps, such as a vacuum precision distillation step and a chromatography step, and at the same time the importance of adding an enzymic treatment step was demonstrated to this end.

Example 3

In order to observe the effectiveness of enzymic treatment as to raw material fat different from the raw material fat used in Examples 1 and 2, experiments of Example 3 and Comparative Example 3 were performed. In order to explicitly show the comparison, concentration and purification of DHA ethyl ester were tracked and EPA ethyl ester was not included.

In Example 3, treatment including an enzymic treatment step completely the same as Example 1 was performed, as will be described below. As for the raw material fat, 100.0 kg Japanese bonito oil (AV 4.2, SDA 3.3 wt %, EPA 5.6 wt %, DHA 28.5 wt %) was used as a starting raw material, and alkali deacidification treatment was performed on the bonito crude oil in accordance with conventional methods, thus obtaining 95.0 kg deacidified bonito oil of AV 0.3.

When treatment including an enzymic treatment step completely the same as Example 1 was performed, the composition of the DHA ethyl ester fraction prior to vacuum precision distillation was SDA-EE 2.1 wt %, EPA-EE wt 4.7%, DHA 47.5 wt %, and 17.9 kg of 96.5 wt % DHA ethyl ester was recovered after chromatography purification (EPA yield 60.1%, POV 3.3).

Comparative Example 3

In order to demonstrate the effects of enzymic treatment in Example 3, an experiment of Comparative Example 3 was performed, where the same experiment as that of Example 3 was performed except for not including an enzymic treatment step.

The deacidified preparation was ethyl-esterified similar to Comparative Example 1, and then the ethyl ester was separated and purified through vacuum precision distillation similar to Patent Document 9 and Comparative Example 1, thus obtaining an intermediate purified product of EPA ethyl ester. The intermediate purified product was further concentrated and purified using a chromatography method (SMB), obtaining the results shown in Table 4. After the final chromatography purification, 15.8 kg of 99.1 wt % DHA ethyl ester was recovered (DHA yield 54.9%, POV 3.1).

TABLE 4

Primary fatty acid compositions in purification processes (wt %)

| | fraction | | |
|---|---|---|---|
| Fatty acid composition | Prior to vacuum precision distillationt | DHA-EE fraction after vacuum precision distillation | DHA-EE fraction after chromatography purification |
| SDA-EE (wt %) | 3.3 | 4.0 | 3.1 |
| EPA-EE (wt %) | 5.6 | 6.9 | 6.4 |
| DHA-EE (wt %) | 28.5 | 79.5 | 99.1 |
| Recovery weight (Kg) | 95 | 22.7 | 15.8 |
| DHA yield | 95 | 63.3 | 54.9 |

From the results described above, the effectiveness of reducing the ratio of SDA and EPA, which are factors for decreasing the purity of purification, with respect to DHA was demonstrated in concentration and purification steps, such as a vacuum precision distillation step and a chromatography step, and at the same time the importance of adding an enzymic treatment step was demonstrated to this end.

Example 4

With 100.0 kg Peruvian anchovy oil (AV3.6, SDA 2.9 wt %, EPA 18.3 wt %, DHA 9.0 wt %) as a starting raw material, alkali deacidification treatment was performed in accordance with conventional methods, thus obtaining 94.0 kg deacidified anchovy oil with AV 0.5. 100 L ethanol and 1,000 unit/g of lipase (lipase QLM (Meito Sangyo Co., Ltd.), lipase PL (lipase QLM (Meito Sangyo Co., Ltd.) or Lipozyme (Novozymes)) were added to the deacidified anchovy oil, followed by stirring at 40° C., and the reaction was stopped after about 24 hours later. The reaction liquid was extracted with 200 L hexane, followed by washing with ethanol and water. The aqueous layer (lower layer) was discarded. The upper layer (hexane layer) was dehydrated with anhydrous sodium sulfate, and then concentrated using an evaporator.

The concentrate was subjected to a column that was filled with alumina, and an eluate obtained by using hexane was recovered (ethyl-esterified free fatty acid fraction) and an eluate obtained by using diethyl ether was recovered (glyceride fraction). The recovered liquid was concentrated using an evaporator, and was recovered as respective fractions. A 65.0 kg glyceride fraction and a 26.0 kg ethyl-esterified free fatty acid fraction were obtained.

Analysis of fatty acid compositions was performed using Iatroscan MK-6S from Mitsubishi Kagaku Medience Corp. As described above, the composition was stirred at 40° C. and its reaction was stopped after about 24 hours. Two percent by volume of the hexane solution (1 μL) of the oil recovered after the stopping was spotted on a silica gel rod, followed by developing for 30 minutes with hexane:diethyl ether:acetic acid (90:10:1, volume ratio). Then, the analysis was performed using thin-film chromatography/FID. The results are as follows.

TABLE 5

|    | Initial value | QLM  | PL   | Lipozyme |
|----|---------------|------|------|----------|
| MG | 3.6           | 33.2 | 5.9  | 7.1      |
| DG | 0             | 34.0 | 37.4 | 7.3      |
| TG | 96.4          | 4.8  | 44.4 | 82.6     |
| EE | 0             | 28.1 | 12.3 | 2.9      |

*note that the numbers in the Table represent composition % by TLC/FID.

MG: monoglycerol

DG: monoglycerol

TG: monoglycerol

EE: ethyl-esterification

Results of chromatography analysis on the EE fraction (ethyl-esterified fraction) are as follows:

Gas chromatography was performed using GC-2010plus from Shimadzu Corp. With regard to capillary columns and the like, the analysis was performed with the following conditions: DB-WAX (Agilent Technologies), 0.25 mmID× 30 m, 0.25 μm film thickness, carrier gas: helium, detector: 260° C., FID, inlet: 250° C., split ratio 1:1, injection rate 1.5 μL, column temperature: 210° C.

GC analysis procedures are as follows. The ethyl ester fraction of fatty acid was stirred at 40° C. and 5 μL oil recovered about 24 hours later was dissolved into 1 mL hexane, followed by analyzing using the GC. With regard to the glyceride fraction, the 16.7 μL glyceride fraction was dissolved into 2 μL hexane, and 2 μL saturated potassium hydroxide aqueous solution was added to perform methylation. Washing with saturated salt water and then centrifugation were performed, and the hexane layer was dehydrated with anhydrous sodium sulfate. Then analysis was performed using the GC.

TABLE 6

|                  | Initial value | EE fraction | Glyceride fraction |
|------------------|---------------|-------------|--------------------|
| Myristic acid    | 7.7           | 8.0         | 6.0                |
| Palmitic acid    | 18.4          | 23.5        | 11.4               |
| Palmitoleic acid | 9.4           | 11.7        | 7.2                |
| Stearic acid     | 3.2           | 5.4         | 1.3                |
| Oleic acid       | 10.2          | 15.1        | 6.5                |
| Elaidic acid     | 3.0           | 5.3         | 1.1                |
| Linoleic acid    | 0.99          | 0.31        | 0.45               |
| α-linolenic acid | 0.55          | 0.82        | 0.30               |
| SDA              | 2.9           | 4.4         | 1.3                |
| AA               | 0.96          | 0.0         | 1.8                |
| ETA              | 0.82          | 1.1         | 0.5                |
| EPA              | 18.3          | 3.9         | 36.3               |
| DPA              | 1.7           | 0.0         | 2.7                |
| DHA              | 9.0           | 2.8         | 13.1               |

According to conventional methods, 64.0 kg ethyl-esterified glyceride was obtained from the glyceride fraction using an alkali catalyst method.

Both of the ethyl ester obtained from the glyceride fraction and the ethyl ester obtained from the free fatty acid fraction were separated and purified using a vacuum precision distillation method in reference to Cited Reference 9, thus obtaining the products in Table 7.

TABLE 7

|                        | Glyceride fraction |                | Free fatty acid fraction |                |
|------------------------|--------------------|----------------|--------------------------|----------------|
| Fatty acid composition | (1) DHA-EE fraction | (2) EPA-EE fraction | (3) DHA-EE fraction | (4) EPA-EE fraction |
| SDA-EE (wt %)          | 0.4                | 2.9            | 0.4                      | 6.1            |
| EPA-EE (wt %)          | 6.3                | 89.7           | 1.6                      | 70.3           |
| DHA-EE (wt %)          | 60.8               | 2.4            | 51.8                     | 2.2            |
| Recovery weight (Kg)   | 9.0                | 20.1           | 0.4                      | 1.1            |

From the respective fraction products, 9.4 kg DHA ethyl ester (DHA-EE) fraction obtained by mixing (1) and (3) (SDA 0.4%, EPA 4.1%, DHA 60.4%) and 21.2 kg EPA ethyl ester (EPA-EE) fraction obtained by mixing (2) and (4) (SDA 3.1%, EPA 88.7%, DHA 2.4%) were prepared.

The DHA ethyl ester fraction and EPA ethyl ester fraction were respectively treated using simulated moving bed chromatography (SMB). Reversed phase (ODS) columns (four C18 columns were used) were attached and methanol was used for an eluent.

As a result, 5.5 kg of 96.1 wt % DHA ethyl ester (58.7% DHA yield, POV 3.9) was recovered from the DHA ethyl ester fraction, and 14.2 kg of 98.3 wt % EPA ethyl ester was recovered from the EPA ethyl ester fraction 76.3% EPA yield, POV 3.5).

1.0 wt % activated white earth was added to each of the DHA ethyl ester and EPA ethyl ester described above, and each ester was stirred at 40° C. for an hour under reduced pressure, and thereafter, a preparation was obtained through suction filtration in the presence of nitrogen gas. The yield at this time was 99.0 wt % (POV 0.5) for both.

0.2 wt % DL-α-tocopherol was added to these purified preparations, followed by mixing and dissolving under nitrogen gas flow, thus obtaining a product.

As described above, the present invention is exemplified by the use of its preferred Embodiments. However, the present invention should not be interpreted solely based on the subject Embodiments. It is understood that the scope of the present invention should be interpreted solely based on the claims. It is understood that those skilled in the art are able to carry out an equivalent scope from the description of specific preferred Embodiments and based on the description of the present invention and common general knowledge. Furthermore, it is understood that any patent, any patent application and any references cited in the present specification should be incorporated by reference in the present specification in the same manner as the contents are specifically described therein.

INDUSTRIAL APPLICABILITY

According to the present invention, provided is a method for obtaining a ω3 fatty acid ethyl ester, such as EPA and DHA, each as a high purity product at a high yield. The present invention makes it possible to provide a less expensive and high purity ω3 fatty acid ethyl ester, such as EPA and DHA.

The invention claimed is:

1. A method for preparing an eicosapentaenoic acid ethyl ester and a docosahexaenoic acid ethyl ester from a raw material fat comprising eicosapentaenoic acid and docosahexaenoic acid, the method comprising the steps of:

(a) treating the raw material fat with a lipolytic enzyme to obtain a treated substance;
(b) fractionating the treated substance of step (a) into a glyceride fraction and a free fatty acid fraction;
(c) ethyl-esterifying each of the glyceride fraction and the free fatty acid fraction obtained in step (b) as needed to obtain an ethyl-esterified glyceride fraction and an ethyl-esterified free fatty acid fraction;
(d) purifying and fractionating the ethyl-esterified glyceride fraction into:
  (1) a first fraction of the ethyl-esterified glyceride fraction comprising more docosahexaenoic acid ethyl ester than the ethyl-esterified glyceride fraction prior to the step (d) of purifying and comprising less eicosapentaenoic acid ethyl ester than the ethyl-esterified glyceride fraction prior to the step (d) of purifying; and
  (2) a second fraction of the ethyl-esterified glyceride fraction comprising more eicosapentaenoic acid ethyl ester than the ethyl-esterified glyceride fraction prior to the step (d) of purifying and comprising less docosahexaenoic acid ethyl ester than the ethyl-esterified glyceride fraction prior to the step (d) of purifying;
(e) purifying and fractionating the ethyl-esterified free fatty acid fraction into:
  (3) a first fraction of the ethyl-esterified free fatty acid fraction comprising more docosahexaenoic acid ethyl ester than the ethyl-esterified free fatty acid fraction prior to the step (e) of purifying and comprising less eicosapentaenoic acid ethyl ester than the ethyl-esterified free fatty acid fraction prior to the step (e) of purifying; and
  (4) a second fraction of the ethyl-esterified free fatty acid fraction comprising more eicosapentaenoic acid ethyl ester than the ethyl-esterified free fatty acid fraction prior to the step (e) of purifying and comprising less docosahexaenoic acid ethyl ester than the ethyl-esterified free fatty acid fraction prior to the step (e) of purifying;
(f) mixing the fraction (1) of step (d) with the fraction (3) of step (e) to obtain a first mixture;
(g) mixing the fraction (2) of step (d) with the fraction (4) of step (e) to obtain a second mixture;
(h) further purifying the first mixture of step (f) to obtain a purified substance comprising a docosahexaenoic acid ethyl ester; and
(i) further purifying the second mixture of step (g) to obtain a purified substance comprising an eicosapentaenoic acid ethyl ester.

2. A method for preparing an eicosapentaenoic acid ethyl ester and a docosahexaenoic acid ethyl ester from a raw material fat comprising eicosapentaenoic acid and docosahexaenoic acid, the method comprising the steps of:
(a) treating the raw material fat with a lipolytic enzyme to obtain a treated substance, which takes place under conditions for ethyl-esterifying fatty acids;
(b) fractionating the treated substance of step (a) into a glyceride fraction and an ethyl-esterified free fatty acid fraction;
(c) ethyl-esterifying the glyceride fraction obtained in step (b), to obtain an ethyl-esterified glyceride fraction;
(d) purifying and fractionating the ethyl-esterified glyceride fraction into:
  (1) a first fraction of the ethyl-esterified glyceride fraction comprising more docosahexaenoic acid ethyl ester than the ethyl-esterified glyceride fraction prior to the step (d) of purifying and comprising less eicosapentaenoic acid ethyl ester than the ethyl-esterified glyceride fraction prior to the step (d) of purifying; and
  (2) a second fraction of the ethyl-esterified glyceride fraction comprising more eicosapentaenoic acid ethyl ester than the ethyl-esterified glyceride fraction prior to the step (d) of purifying and comprising less docosahexaenoic acid ethyl ester than the ethyl-esterified glyceride fraction prior to the step (d) of purifying;
(e) purifying and fractionating the ethyl-esterified free fatty acid fraction into:
  (3) a first fraction of the ethyl-esterified free fatty acid fraction comprising more docosahexaenoic acid ethyl ester than the ethyl-esterified free fatty acid fraction prior to the step (e) of purifying and comprising less eicosapentaenoic acid ethyl ester than the ethyl-esterified free fatty acid fraction prior to the step (e) of purifying; and
  (4) a second fraction of the ethyl-esterified free fatty acid fraction comprising more eicosapentaenoic acid ethyl ester than the ethyl-esterified free fatty acid fraction prior to the step (e) of purifying and comprising less docosahexaenoic acid ethyl ester than the ethyl-esterified free fatty acid fraction prior to the step (e) of purifying;
(f) mixing the fraction (1) of step (d) with the fraction (3) of step (e) to obtain a first mixture;
(g) mixing the fraction (2) of step (d) with the fraction (4) of step (e) to obtain a second mixture;
(h) further purifying the first mixture of step (f) to obtain a purified substance comprising a docosahexaenoic acid ethyl ester; and
(i) further purifying the second mixture of step (g) to obtain a purified substance comprising an eicosapentaenoic acid ethyl ester.

3. The method of claim 1, wherein one or more of:
(1) the raw material fat is a deacidified raw material fat,
(2) the raw material fat is a deacidified raw material fat that has an acid value of 3 or less,
(3) the raw material fat comprises 4 wt % or more eicosapentaenoic acid and 4 wt % or more docosahexaenoic acid, and
(4) the lipolytic enzyme is a microorganism-derived lipase that selectively hydrolyzes positions 1 and 3 of triglyceride.

4. The method of claim 1, wherein the fractionating in step (b) comprises a method selected from falling thin-film molecular distillation, centrifugal molecular distillation, and an elution method.

5. The method of claim 4, wherein the fractionating in step (b) comprises the elution method, wherein a first eluate obtained by elution with hexane is recovered as an ethyl-esterified free fatty acid fraction, and wherein a second eluate obtained by elution with diethyl ether is recovered as a glyceride fraction.

6. The method of claim 1, wherein either or both of:
(1) the step (c) of ethyl-esterifying at least one fraction that comprises glycerides comprises an alkali catalyst method or an enzymic method, and/or
(2) the step (c) of ethyl-esterifying at least one fraction that comprises free fatty acids fraction comprises an acid catalyst method or an enzymic method.

7. The method of claim 1, wherein the purifying in step (d) comprises a method selected from vacuum precision distillation, a urea addition method, a silver nitrate complex method, fixed-bed chromatography, and simulated moving bed (SMB) chromatography.

8. The method of claim 1, wherein the purifying in step (e) comprises a method selected from vacuum precision distillation, a urea addition method, a silver nitrate complex method, fixed-bed chromatography, and simulated moving bed (SMB) chromatography.

9. The method of claim 1, wherein the purifying in step (h) comprises a method selected from vacuum precision distillation, a urea addition method, a silver nitrate complex method, fixed-bed chromatography, and simulated moving bed (SMB) chromatography.

10. The method of claim 1, wherein the purifying in step (i) comprises a method selected from vacuum precision distillation, a urea addition method, a silver nitrate complex method, fixed-bed chromatography, and simulated moving bed (SMB) chromatography.

11. The method of claim 1, wherein:
concentration of the docosahexaenoic acid ethyl ester in the first fraction (1) in step (d) is 15 wt % or more;
concentration of the eicosapentaenoic acid ethyl ester in the second fraction (2) in step (d) is 15 wt % or more;
concentration of the docosahexaenoic acid ethyl ester in the first fraction (3) in step (e) is 15 wt % or more; and
concentration of the eicosapentaenoic acid ethyl ester in the second fraction (4) in step (e) is 15 wt % or more.

12. The method of claim 1, wherein:
in the first mixture obtained in step (f), concentration of the docosahexaenoic acid ethyl ester is 15 wt % or more and concentration of the eicosapentaenoic acid ethyl ester is 15 wt % or less, and
in the second mixture obtained in step (g), concentration of the eicosapentaenoic acid ethyl ester is 15 wt % or more and concentration of the docosahexaenoic acid ethyl ester is 15 wt % or less.

13. The method of claim 1, wherein:
in the purified substance obtained in step (h) concentration of the docosahexaenoic acid ethyl ester is 70 wt % or more, and
in the purified substance obtained in step (i) concentration of the eicosapentaenoic acid ethyl ester is 70 wt % or more.

14. The method of claim 1, further comprising the steps of:
(j) treating the purified substance comprising a docosahexaenoic acid ethyl ester obtained in step (h) with an adsorbent to remove impurities to obtain the purified substance comprising a docosahexaenoic acid ethyl ester from which impurities have been removed; and
(k) treating the purified substance comprising an eicosapentaenoic acid methyl ester obtained in step (i) with an adsorbent to remove impurities to obtain the purified substance comprising an eicosapentaenoic acid ethyl ester from which impurities have been removed.

15. The method of claim 14, wherein the adsorbent is selected from the group consisting of acid white earth, activated charcoal, silicic acid and alumina, and wherein after said steps of treating with the adsorbent, the purified substance comprising a docosahexaenoic acid ethyl ester from which impurities have been removed has a peroxide value that is 3 or less and the purified substance comprising an eicosapentaenoic acid ethyl ester from which impurities have been removed has a peroxide value that is 3 or less.

16. The method of claim 14, further comprising the steps of:
(l) adding an antioxidant agent to the purified substance obtained in step (j) comprising a docosahexaenoic acid ethyl ester from which impurities have been removed; and
(m) adding an antioxidant agent to the purified substance obtained in step (k) comprising an eicosapentaenoic acid ethyl ester from which impurities have been removed.

17. The method of claim 16, wherein the antioxidant agent is selected from the group consisting of tocopherol, ascorbyl palmitate, catechin and a rosemary extract.

* * * * *